(12) United States Patent
Lindenberg et al.

(10) Patent No.: US 9,060,740 B2
(45) Date of Patent: Jun. 23, 2015

(54) DENTAL X-RAY DEVICE WITH IMAGING UNIT FOR SURFACE DETECTION AND METHOD FOR GENERATING A RADIOGRAPH OF A PATIENT

(75) Inventors: Kai Lindenberg, Wersau (DE); Christian Beckhaus, Darmstadt (DE); Johannes Ulrici, Darmstadt (DE)

(73) Assignee: Sirona Dental Systems GmbH, Bensheim (DE)

( * ) Notice: Subject to any disclaimer, the term of this patent is extended or adjusted under 35 U.S.C. 154(b) by 140 days.

(21) Appl. No.: 13/821,862
(22) PCT Filed: Sep. 8, 2011
(86) PCT No.: PCT/EP2011/065587
§ 371 (c)(1), (2), (4) Date: Mar. 8, 2013
(87) PCT Pub. No.: WO2012/032132
PCT Pub. Date: Mar. 15, 2012

(65) Prior Publication Data
US 2013/0163718 A1    Jun. 27, 2013

Related U.S. Application Data

(60) Provisional application No. 61/384,476, filed on Sep. 20, 2010.

(30) Foreign Application Priority Data

Sep. 8, 2010 (DE) .......................... 10 2010 040 386

(51) Int. Cl.
*A61B 6/00* (2006.01)
*A61B 5/00* (2006.01)
(Continued)

(52) U.S. Cl.
CPC .............. *A61B 6/582* (2013.01); *A61B 5/0035* (2013.01); *A61B 5/0077* (2013.01);
(Continued)

(58) Field of Classification Search
CPC ....... A61B 6/4441; A61B 6/4458; A61B 6/04
USPC ...................... 378/197, 38–39, 206
See application file for complete search history.

(56) References Cited

U.S. PATENT DOCUMENTS 6,081,739 A    6/2000  Lemchen ............... 600/407
6,574,296 B2   6/2003  Stierstorfer ............. 378/15
(Continued)

FOREIGN PATENT DOCUMENTS

DE           103 17 137 A1    11/2004
DE       10 2004 020 370 B4    11/2005
(Continued)

OTHER PUBLICATIONS

German Examination Report issued by the German Patent Office on Mar. 16, 2011.
(Continued)

*Primary Examiner* — Hoon Song
(74) *Attorney, Agent, or Firm* — Fitzpatrick, Cella, Harper & Scinto (57) ABSTRACT

The invention relates to a dental X-ray system for the creation of a radiograph (13), comprising an imaging unit (5) for surface detection. The imaging unit (5) has a light source (6), which produces a polychromatic beam of visible light (6'), a masking edge (7), which extends at least partially into the polychromatic beam of light (6') between the light source (6) and the recording area (19) for the purpose of creating a shadow demarcation line (17) in said recording area (19), and an optical detector (8), wherein the light source (6), the masking edge (7) and the optical detector (8) are mounted directly on the supporting device (2) and/or on the X-ray source (3) and/or on the X-ray detector (4) and can be moved together therewith past the recording area (19) in circular motion.

21 Claims, 4 Drawing Sheets

(51) Int. Cl.
*A61B 6/14* (2006.01)
*G01B 11/25* (2006.01)
*A61B 6/08* (2006.01)

(52) U.S. Cl.
CPC ............... *A61B 5/0088* (2013.01); *A61B 6/08* (2013.01); *A61B 6/14* (2013.01); *A61B 6/4435* (2013.01); *A61B 6/466* (2013.01); *A61B 6/5235* (2013.01); *A61B 2576/02* (2013.01); *G01B 11/25* (2013.01); *A61B 6/4417* (2013.01); *A61B 6/5247* (2013.01)

(56) References Cited

U.S. PATENT DOCUMENTS

| | | | |
|---|---|---|---|
| 7,372,935 B2 | 5/2008 | Bernhardt et al. | 378/4 |
| 7,551,711 B2 | 6/2009 | Sarment et al. | 378/15 |
| 2004/0258210 A1 | 12/2004 | Ritter | 378/198 |
| 2006/0262894 A1 | 11/2006 | Bernhardt et al. | 378/4 |
| 2006/0274888 A1* | 12/2006 | Bernhardt et al. | 378/117 |
| 2007/0030957 A1* | 2/2007 | Pommi | 378/197 |
| 2007/0297571 A1 | 12/2007 | Beckhaus et al. | 378/147 |
| 2011/0129058 A1 | 6/2011 | Ulrici et al. | 378/4 |
| 2011/0242281 A1 | 10/2011 | Schmidt | 348/46 |

FOREIGN PATENT DOCUMENTS

| | | |
|---|---|---|
| DE | 10 2005 022 540 B4 | 11/2006 |
| DE | 10 2008 022 922 A1 | 11/2009 |
| DE | 10 2008 035 412 A1 | 2/2010 |
| DE | 10 2008 040 947 A1 | 4/2010 |
| WO | WO 2011/076416 A1 | 6/2011 |
| WO | WO 2011/095694 A1 | 8/2011 |

OTHER PUBLICATIONS

Machine English translation of the German Examination Report.

* cited by examiner

DENTAL X-RAY DEVICE WITH IMAGING UNIT FOR SURFACE DETECTION AND METHOD FOR GENERATING A RADIOGRAPH OF A PATIENT

TECHNICAL BACKGROUND

The invention relates to a dental X-ray device for generating a radiograph of a patient, which X-ray device additionally comprises an imaging unit for surface detection. The invention further relates to a method for generating a radiograph of a patient, in which method a system comprising an X-ray source and an X-ray detector is moved so as to rotate around the patient.

PRIOR ART

A plurality of X-ray devices comprising an additional optical imaging unit and methods for operating such devices are known in the prior art.

DE 10 2004 020 370 B4, for example, discloses an X-ray emitter comprising an imaging unit adapted for light waves in the visible range and disposed in or on the housing.

DE 10 2008 035 412 A1 discloses an X-ray device comprising an optical camera disposed on the X-ray device. An image of a patient positioned in the X-ray device is created by means of the camera and processed to form a picture. On the basis of this pictorial representation, the setting and/or control data for producing a radiograph are monitored and altered before the radiograph is generated.

U.S. Pat. No. 7,551,711 B2 likewise describes an X-ray device comprising an optical camera disposed on the X-ray device, the optical data being generated simultaneously with the radiograph, and a surface image of the patient produced from the optical data is provided for improved interpretation of the radiographs.

U.S. Pat. No. 6,574,296 B2 likewise discloses an X-ray device comprising an optical recording device, the optical data being acquired during the creation of the radiograph.

U.S. Pat. No. 6,081,739 discloses an X-ray device comprising an ultrasonic or optical detector and a color video detector for simultaneously producing a radiograph, an elevation profile and a color video image. Instead of using an ultrasonic or optical detector for determining the surface data, a 3D color scanner can alternatively be used that acquires both color data and surface data.

One disadvantage of these methods and devices is that there is no provision made for active illumination, due to which the robustness, precision and completeness of the picture are adversely affected.

DE 10 2005 022 540 B4 discloses an X-ray device comprising an optical sensor, the surface detected by the optical sensor being used in order to supplement missing image data during the reconstruction of the projected images produced by means of the X-ray device to form a 3D radiograph. The optical sensor comprises a light source and a camera, a striped pattern being projected by the light source onto the patient from a first direction, while the light backscattered by the patient is recorded by the camera from another direction so that the surface can be determined by the triangulation method.

DE 103 17 137 A1 also discloses an X-ray device comprising an additional 3D sensor and a light source for generating an image dataset of at least a part of the surface of the patient, the light of the light source being projected linearly onto the patient by means of a pivotal deflection mirror, while the image data are recorded at the same time as the creation of the radiograph.

One disadvantage of this method is that it is not possible to obtain any color or brightness information of the patient. There is no advantage to be gained from the production of a line of light by means of a point light source or an at least small-area light source and a pivotal deflecting device, since shadowing effects or non-illuminated regions of the line can result on the surface of the patient, which can lead to incomplete datasets.

It is therefore an object of the present invention to provide a method for the robust, accurate and simultaneous acquisition of a dental tomographic dataset of a patient and a colored elevation profile of the face of a patient with open eyes, which colored elevation profile can be combined with the tomographic dataset, and a device for carrying out this method.

SUMMARY OF THE INVENTION

The invention relates to a dental X-ray device for generating a radiograph of a patient, which dental X-ray device comprises an X-ray source and an X-ray detector that are each disposed on a supporting device and can be moved, at least in part, by means of the supporting device around a recording area located between the X-ray source and the X-ray detector, and at least one imaging unit for detecting the surface of a patient positioned in the recording area. The imaging unit comprises at least one light source that generates a polychromatic beam of visible light directed toward the recording area. The imaging unit further comprises at least one masking edge that extends, at least in part, into the light beam between the light source and the recording area to produce a shadow demarcation line in the recording area. The imaging unit further comprises at least one optical detector. The at least one light source, the at least one masking edge and the at least one optical detector are disposed directly on the supporting device and/or the X-ray source and/or the X-ray detector and can be moved together with the X-ray source and the X-ray detector in circular motion past the recording area. The positions of the at least one light source, the at least one masking edge and the at least one optical detector relative to each other are known.

The recording area is a space that is disposed between the X-ray source and the X-ray detector within the X-ray device and that includes at least the regions to be scanned, that is, the volume to be scanned for the radiograph and the regions to be imaged to give the surface and color information.

The optical data that can be generated in addition to the radiograph, namely the surface data and color data that can be acquired due to the provision of an imaging unit, can facilitate the orientation and thus also the interpretation of the radiograph.

As a result of the at least one masking edge extending into the beam path directed toward the recording area, a light-colored region and a dark-colored region are formed in the recording area, for example on the head of a patient positioned therein. A line or shadow demarcation line in the form of a borderline between the light-colored and dark-colored regions thus extends at least over parts of the head of the patient. Depending on the orientation of the masking edge, this shadow demarcation line can extend, for example, in the vertical direction over a part or all of the patient's head to be scanned.

The provision, according to the invention, of an imaging unit comprising a masking edge for producing a shadow demarcation line makes it possible to use structured light for scanning the object. The term "structured light" used here is to be understood to mean light which, in its extension in space, has a structure in the sense of light-colored and dark-colored regions. For example, this type of structured light can be a pattern, a stripe or a line that imparts structure to the light in a direction extending transversely to its direction of propagation. As compared with a scanning process carried out with the use of unstructured light, that is, with homogeneous illumination of the object to be scanned, a scanning process carried out by means of structured light is usually more robust and requires less processing time.

A single masking edge is not an instance of a grid or even a projector comprising a freely selectable pattern, as mentioned, for example, in DE 10 2008 022 922 A1 as an exemplary embodiment, but rather it is particularly important for a recorded camera raw image to be uniformly illuminated over a defined area of maximum size, that is to say, with no abrupt brightness changes as in the case of a grid. This area serves for acquisition of the color information of the object without it being necessary to switch the light source or the projected pattern or a masking edge on or off. Moreover, this area can serve to increase the geometrical accuracy in a further analysis step involving standard stereoisometric methods. The use of a grid in the recorded images would significantly limit the quality of the surface model both as regards the accuracy of the geometry and with respect to color fidelity and the lack of influence of the illumination on the color information. Detection of the shadow demarcation edge in the recording is particularly reliable and simpler than the detection of a grid or some other pattern.

The light which originates directly from the masking edge, delimits an illuminated region, and extends toward the shadow demarcation line, for example, toward an object to be scanned in the recording area, i.e. which forms the shadow demarcation line, is referred to hereinafter as the illuminating demarcation beam.

The light that originates directly from the shadow demarcation line and extends toward the optical detector is accordingly referred to as the monitoring demarcation beam.

Since the positions of the at least one light source, the at least one masking edge and the at least one optical detector are known and these positions are fixed in relation to each other, a fixed angle is formed between the illuminating demarcation beam and the monitoring demarcation beam. From this angle, which can be measured for example, surface data can be computed by the triangulation method on the basis of the progression of the shadow demarcation line, and the base length required for the calculation is the distance from the camera to the demarcation beam.

The use of polychromatic light makes it possible to additionally detect color data from the recordings made by the imaging unit described above. For this purpose, one or more polychromatic light sources such as one or more LEDs having a polychromatic emission spectrum can be used. It is also possible to combine a plurality of monochromatic light sources to produce a polychromatic light beam.

The optical detector can, for example, be a color sensor for detecting the color data and an additional detector for detecting the surface data. It is thus possible to select detector settings that provide optimum detection of surface data and color data that can be clearly distinguished from each other.

Alternatively, one or more color sensors can be used for detecting the surface data and the color data so that both data sets can be measured in the same coordinate system.

If a plurality of sensors is used in this way, then the points located particularly in the light-colored region adjoining the shadow demarcation line are detected from a plurality of angles. As a result of the redundancy of points in the images, the accuracy of the surface data can be significantly increased by an additional comparison of different perspectives. Methods based on parallax, such as stereo correspondence, can be used as such a stereometric method, for example.

A correlation between the optical data generated by the imaging unit and the radiograph can be established, since the imaging unit is fixed to the movable part of the X-ray device and it records concurrently with the creation of the radiograph.

Furthermore, this fixed relationship, particularly of the light source and the masking edge, ensures that a patient positioned in the recording area can foresee any change in the illumination during X-raying, as a result of which he or she will be pacified and kept from moving by reflex while being scanned.

The X-ray device can be an orthopantomograph or a computer tomography scanner, for example, and the radiographs produced by the X-ray device can accordingly be a tomographic image or a 3D X-ray image.

Advantageously, the light source can be a linear light strip comprising one or more individual juxtaposed light sources.

By means of a light source extending linearly in the vertical direction, it is possible to ensure homogeneous and adequate illumination of the patient in the vertical direction. This ensures that the shadow demarcation line is clearly formed in the vertical direction, for example, over the entire face of a patient positioned in the recording area.

Advantageously, the at least one light source can have a maximum luminous intensity of 5 $lm/cm^2$.

As a result, it is possible to scan the head of a patient with his or her eyes open, without having to provide additional protection for the patient's eyes.

Advantageously, the optical detector can register both brightness information and color information and present these as a recording, also referred to as a camera raw image.

It is advantageous when there is an area in the recording that is free from the shadow caused by the masking edge to an extent of more than 50%, preferably more than 75% and more preferably more than 85%. This has the advantage that a large area can be used for the acquisition of angle-dependent color data and possibly for the use of stereometric methods.

The invention further relates to a method for producing a radiograph of a patient by means of an X-ray device, in which method X-ray radiation is used during an at least partial rotation of a system comprising an X-ray source and an X-ray detector surrounding a recording area located between the X-ray source and the X-ray detector so that X-rays that are produced by the X-ray source and that pass through the recording area can be detected by the detector from a plurality of different directions. Concurrently with the creation of the radiograph, at least one masking edge is imaged in the recording area by a polychromatic light beam emitted by at least one light source of an imaging unit that moves together with the system during an at least partial rotation of the system in such a way that a light-colored region and a dark-colored region are formed that adjoin each other linearly so that a shadow demarcation line is formed and that at least parts of the light-colored and dark-colored regions and the shadow demarcation line are recorded by at least one optical detector, and color data and surface data are acquired from the recordings made by the optical detector, the at least one light source, the at least one masking edge, and the at least one optical detector employed for carrying out the method are located at known positions on the X-ray device.

The radiograph can, for example, be a 3D X-ray image that is reconstructed from individual projection images, or is alternatively a tomographic image.

The additional data can facilitate orientation and thus also the interpretation of the radiograph.

The projection of a masking edge results in a light-colored and a dark-colored region being formed on the patient, and these regions adjoin each other linearly. The borderline thus formed is referred to as the shadow demarcation line. The part of the patient that is to be X-rayed is thus not uniformly illuminated, but instead a structure, namely a shadow demarcation line, is formed on the patient by means of light. Therefore, reference is also made to the use of structured light in this context. Such a method is usually robust and requires less processing power than methods carried out without the use of structured light, that is, methods operating with purely homogeneous illumination.

The projection of the masking edge by means of polychromatic light makes it possible to acquire both surface data and color data at the same time.

The surface data can be acquired by the triangulation method from the progression of the shadow demarcation line that is in the form of a linear border between the light-colored and dark-colored regions and is detected in the recordings made by the imaging unit. This is particularly possible due to the fact that the positions of the light source, the masking edge and the optical detector are known, from which the base length and the angle for triangulation can be determined.

As a result of the projection of the masking edge by the use of polychromatic light, the light backscattered by the surface of a patient positioned in the recording area also includes color information of the patient in addition to the brightness information. The color information is detected additionally by means of the recordings made by the imaging unit. For this purpose, for example, a color sensor can be used as the optical detector. It is also possible, for example, to use a color sensor for acquiring the color data and an additional sensor that is sensitive, for example, in a narrower wavelength range for detecting the shadow demarcation line.

A correlation between the optical data generated by the imaging unit and the radiograph can be established, since the imaging unit is fixed to the movable part of the X-ray device and it records concurrently with the creation of the radiographs.

Furthermore, this fixed arrangement particularly of the light source and the masking edge ensures that a patient positioned in the recording area can foresee any change in the illumination during X-raying, as a result of which he or she will be pacified and kept from moving by reflex while being scanned.

The method employed in order to obtain a colored surface model after the data have been acquired comprises at least two stages. In the first stage, the position of the shadow demarcation line on the camera sensor is determined for each image and is transferred to a geometric surface model together with the position of the sensor and the illuminating unit, as determined, for example, by calibration. In the second step, iteration is carried out over all points, also referred to as vertices, of the surface model, and the color information obtained from a number of camera raw images is saved for each point, also referred to as a vertex. Each camera raw image contains the color information of each vertex for a specific illumination angle. In this way there is obtained, as sum, an angle-dependent color information for each point on the surface model.

Unlike the results obtained by the use of a shadow demarcation line, a grid would strongly reduce the angular multiplicity and there would be less information available for the production, on the one hand, of a high-quality illumination-independent image and, on the other hand, of a realistic artificial illumination, with the aid of the color data.

Advantageously, the color data and the surface data can be acquired at a number of successive points in time during the at least partial rotation of the system.

The greater the number of recordings made by the imaging unit during the at least partial rotation of the system, the greater the accuracy of the surface and color data. Furthermore, movements of the patient can be detected in the optical data.

Advantageously, the color data and the surface data can be acquired from at least four different directions. The acquisition of surface data and color data from as many directions as possible results in an increase in the accuracy of these data.

Advantageously, the color data and the surface data can be acquired from directions that are distributed uniformly, in terms of the angular position, throughout the at least partial rotation of the system.

Due to the uniform distribution of the directions from which the data are acquired in terms of the angle of rotation, the data acquired result directly in a uniform surface model. For example, every shadow demarcation line recorded corresponds to a line in the surface model.

Advantageously, the color data and the surface data can be acquired successively at equal time intervals during the at least partial rotation of the system.

The recording of surface and color data at equal time intervals is particularly easy to carry out from a technological viewpoint. The equal time intervals between the recordings at a constant angular speed of rotation have the result that the directions from which the data are acquired are equally distributed, in terms of angle, throughout the rotation of the system. However, not all radiographs can be produced at a constant angular speed of rotation. For example, it should be noted that the angular speed for producing a tomographic image is usually not constant.

Advantageously, a radiograph and surface and color data of a calibration block provided in the X-ray device or inserted therein for this purpose can be generated and the position of the color data and surface data relative to the radiograph determined prior to making a recording or a series of recordings.

The insertion of a calibration block or the use of a calibration block provided in the recording area makes it possible to determine in a simple manner the positions of the color data and surface data relative to the radiograph.

Calibration blocks that are suitable for this purpose are known in the prior art.

Such a calibration block can, for example, be in the form of an independent body that is disposed inside the recording area only for the purpose of calibration, for example due to attachment thereof to a component of the X-ray device. The calibration block can also be a body that is permanently disposed on a component of the X-ray device located in the recording area. It is also possible for the calibration block to be a two-dimensional image, for example, an imprint disposed on a component of the X-ray device located in the recording area.

Advantageously, the color data, surface data, and the radiograph can be transferred to a common coordinate system by means of transformation based on the positions of the color data and the surface data relative to the radiograph.

It is thus possible to combine the surface data and the color data with the radiograph and, for example, to facilitate orientation in the radiographic data. If the radiograph is a tomographic image, it will then be possible, for example, for a 3D coordinate system to serve as a common coordinate system, in which the tomographic image takes up a curved region. It is also possible, for example, to select the 2D coordinate system of the tomographic image as the common coordinate system.

Advantageously, the color data and the surface data of the patient can be displayed jointly with the radiograph.

It is possible to display the data acquired in different juxtaposed windows, for example, a colored surface being displayed in one window and the radiograph in another. It is also possible to present all the data collectively in a single window.

Advantageously, the color data and the surface data of the patient and the radiograph can be simultaneously displayed in a common coordinate system.

The direct correlation between the recordings of the color and surface data and the radiograph can thus be established, so that, for example, the interpretation of the radiograph will be facilitated. For this purpose, the data can be superimposed such that when zooming in on the radiograph from the point of view of the observer, a seamless transition between the one dataset and the other can be effected. It would also be possible to display the color and surface data in a transparent form such that the radiograph displayed in the same coordinate system becomes visible through the color and surface data.

Advantageously, a radiograph and surface data and color data of a calibration block that is present in the X-ray device or is inserted therein for this purpose can be generated and a color correction defined prior to the creation of a recording or series of recordings.

By means of such calibration of the system with regard to color, it can be ensured that the recordings do not show any color cast. For this purpose, color correction is used to allow for the ambient lighting, in particular. Calibration blocks that are suitable for carrying out such a color calibration are known in the art.

Advantageously, a geometric model of the surface can be produced from at least two recordings by means of a stereometric method, the surface data being employed for execution of the stereometric method.

The geometric resolution of the surface model can be improved by using the recordings, preferably only the illuminated area of each of the recordings, for stereometric purposes. In stereometric methods, the position of a point on the imaged object is identified in two images and traced back to the precise position in space with the aid of the know position of the camera sensors. The long time taken for the algorithm to proceed to completion in stereometric methods can be significantly shortened by using the geometric model obtained with the aid of the shadow demarcation line as the starting value for optimization of the stereometric method.

Advantageously, the resolution of the geometric surface model obtained by means of the stereometric method can be higher than the resolution of the surface data.

Due to the multiplicity of recordings, also referred to as camera raw images, there is obtained a large quantity of information to effect a multifold increase in the geometric accuracy as compared with the surface model.

BRIEF DESCRIPTION OF THE DRAWINGS

The invention is described with reference to the drawings, in which.

EXEMPLARY EMBODIMENT

Figure 1:
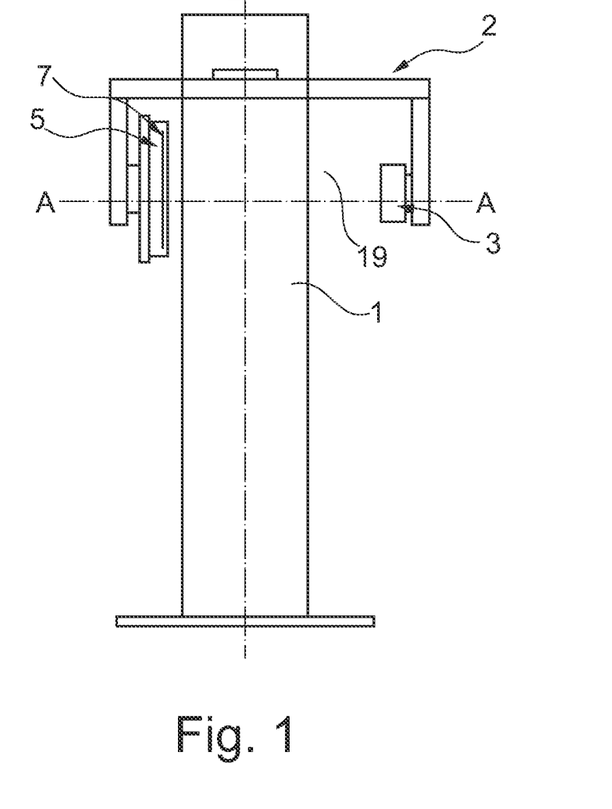
FIG. 1 shows a dental X-ray device of the invention.
Figure 2A:
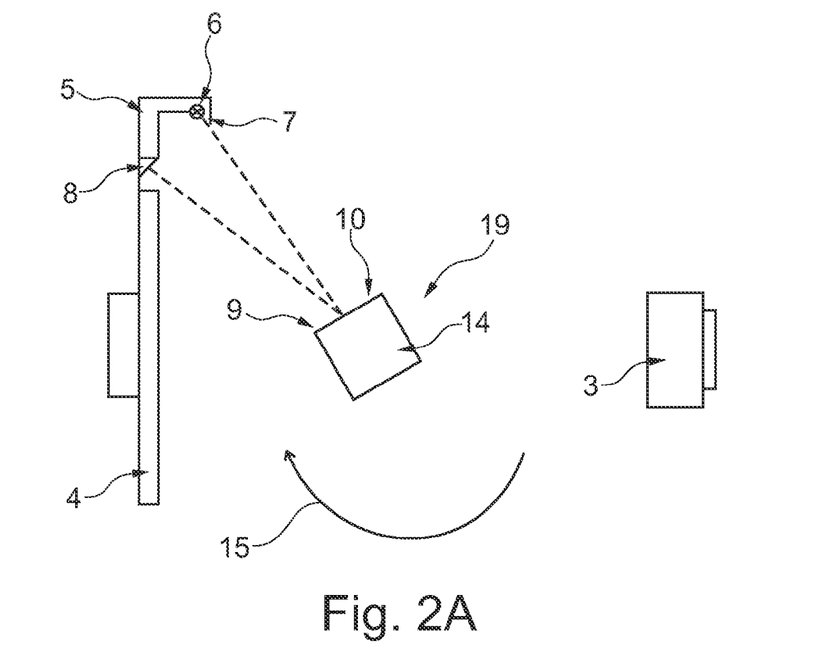
FIGS. 2A and 2B show a horizontal cross-section taken along the line A-A marked in FIG. 1 and a calibration block positioned in the X-ray device.

FIG. 1 is a side view of a dental X-ray device of the invention, and FIG. 2A shows a cross-section of this dental X-ray device taken along the line A-A.

The X-ray device of the invention comprises a holder 1 in the form of, say, a column as shown in FIG. 1. The holder could alternatively be in the form of a wall holder, such as an arm mounted on a wall so as to extend horizontally.

A supporting device 2 is movably mounted on the holder 1. The supporting device 2 is in the form of a horizontal arm that is mounted on the holder 1 for rotation in a horizontal plane about an axis of rotation D. The supporting device 2 is also referred to hereinafter as the supporting arm 2.

An X-ray source 3 and an X-ray detector 4 are disposed on the rotatable supporting arm 2 such that they are located opposite each other and at a distance from each other, with the path of the X-rays extending from the X-ray source 3 to the X-ray detector 4. A recording area 19 is located between the X-ray source 3 and the X-ray detector 4. The recording area 19 encompasses at least the recording areas of the scanning units, that is to say, a volume which can be recorded by the X-ray source and the X-ray detector, and a recording area that can be recorded by the imaging unit. A patient 16 is positioned for scanning in such a way that a region to be scanned such as a portion of the head is located within the recording areas in the recording area 19.

Furthermore, an imaging unit 5 comprising at least one light source 6, at least one masking edge 7, and at least one optical detector 8 is disposed on the X-ray detector 4.

Figure 3A:
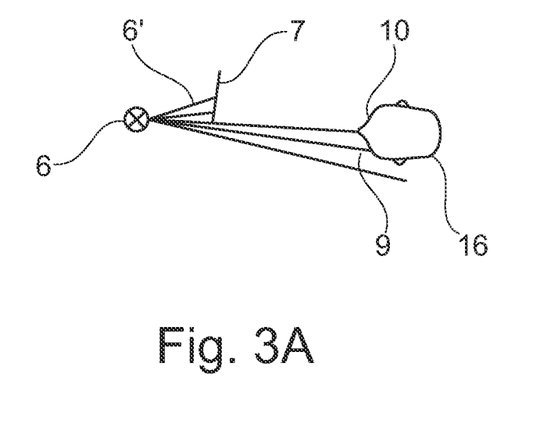
FIGS. 3A and 3B show the principle of projecting a shadow demarcation line.
Figure 3B:
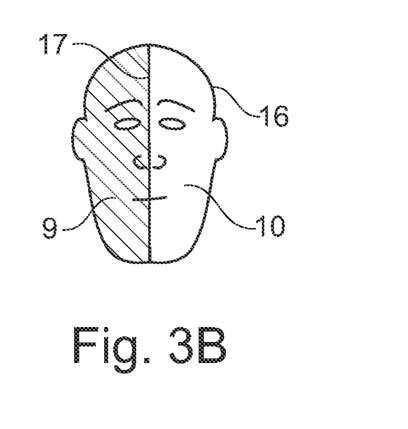

The at least one light source 6 for producing a polychromatic light bundle 6' and the at least one masking edge 7 are positioned such that the at least one masking edge 7 extends, at least partially, into the path of the polychromatic light bundle 6' originating from the at least one light source 6 and directed toward the patient 16, such that a dark-colored region 10 that is masked by the masking edge and a light-colored region 9 that is illuminated by the light of the light source are formed on the patient 16 positioned in the recording area 19, as shown in FIGS. 3A and 3B. This results in a line 17 forming as a borderline between the brighter region 9 and the darker region 10. This line 17 is also referred to as the shadow demarcation line 17.

The at least one optical detector 8 is positioned such that it detects at least this line or shadow demarcation line 17 that is formed on the patient 16.

For the purpose of producing a radiograph 13 of a patient 16 positioned in the recording area 19 of the dental X-ray device, the supporting arm 2 is rotated so that the X-ray detector 4 and the X-ray source 3 move past the patient 16 along a direction of motion 15, and X-rays emitted by the X-ray source 3 and at least partially passing through the patient 16 are recorded by the X-ray detector 4 during such rotation.

At the same time as the production of the radiograph 13, the surface data 11 and color data 12 of the patient 16 are generated by means of the at least one light source 6, the at least one masking edge 7 and the at least one optical detector 8 during this rotation of the supporting arm 2 in that the position of the shadow demarcation line 17 projected onto the patient 1 by the light source 6 and the masking edge 7 is moved relatively to the patient by the rotation of the supporting arm 2 during an at least partial rotation of the system, and the shadow demarcation line 17 is recorded by the optical detector 8 in at least a few different positions relative to the patient 16.

The surface data 11 are determined from the images produced by the imaging unit 5 by the triangulation method based on the course of the shadow demarcation line 17 produced on the patient 16. For this purpose, the known fixed positions of the at least one light source 6, the at least one masking edge 7, and the at least one optical detector 8 and thus the fixed angle resulting therefrom are implemented.

In addition, in order to obtain color information of the patient 16, the at least one light source 6 produces polychromatic light, namely the polychromatic bundle of light 6', which is polychromatically detected by at least one optical detector 8, for example a color sensor. For this purpose, at least one additional optical detector 8 used for detecting the color data 12 can be provided apart from the at least one optical detector 8 used for detecting the shadow demarcation line 17 and thus the surface data 11. It is alternatively possible to use one or more optical detectors 8, for example color sensors, each adapted to detect surface data 11 and color data 12.

Figure 5:
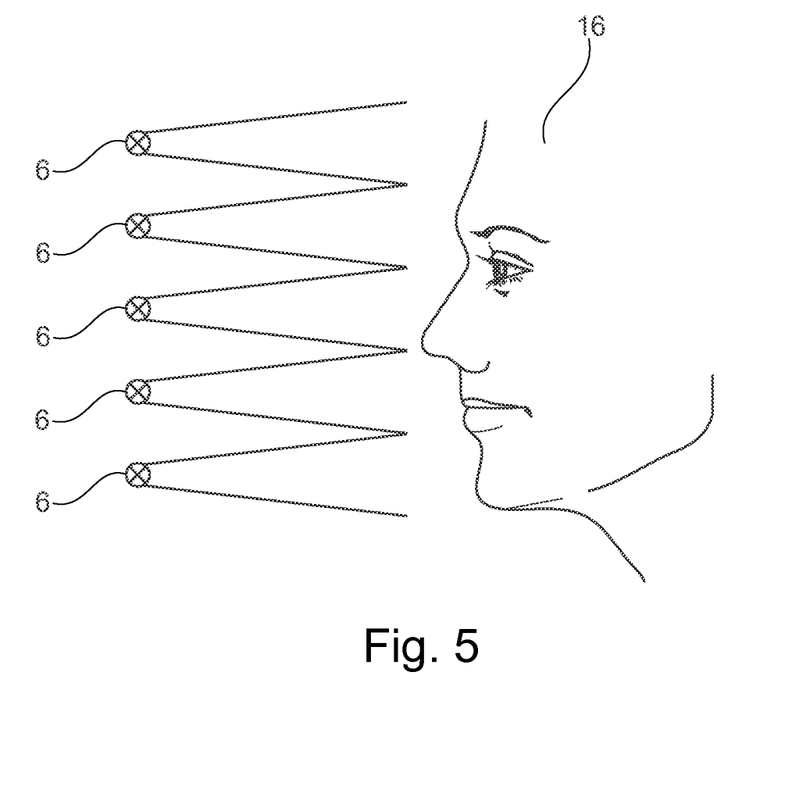
FIG. 5 is an illustration of a plurality of light sources.

The light source 8 used can be composed of LEDs, for example a plurality of LEDs disposed in a vertical row.

One or more light sources having a polychromatic emission spectrum can be used as the light source 6. Alternatively, a plurality of monochromatic light sources that jointly provide the polychromatic bundle of light 6' can serve as the light source 6.

The luminous intensity of the light source 6 is selected such that the patient 6 can keep his or her eyes open when being scanned. Thus no additional safety measures are necessary.

It has been found that surface data 11 and color data 12 of sufficient quality can be acquired when the luminous intensity of the light source 6 is only equal to 30% of that of the ambient light. Surface data 11 and color data 12 of good quality are acquired especially when the light source 6 has a luminous intensity that is from 10 to 100 times stronger than the ambient light. The quality, robustness, and the speed at which images are created essentially depend on the luminous intensity of the light source.

The light source 6, the masking edge 7, and the optical detector 8 can alternatively be disposed on the X-ray source 3 or directly on the supporting arm 2. All of these specifications ensure that the light source 6, the masking edge 7 and the optical detector 8 of the imaging unit 5 move together with the system during at least partial rotation thereof.

As a result, the movement thereof, essentially the movement of the light source 6, is predictable. This helps a patient 16 to keep still and to move his or her eyes as little as possible during imaging, that is, when the system moves through at least a partial revolution. It is thus possible to avoid irritation or reflex movements of the patient 16 when being scanned, which would otherwise lead to a significant loss of quality of a radiograph 13.

Figure 2B:
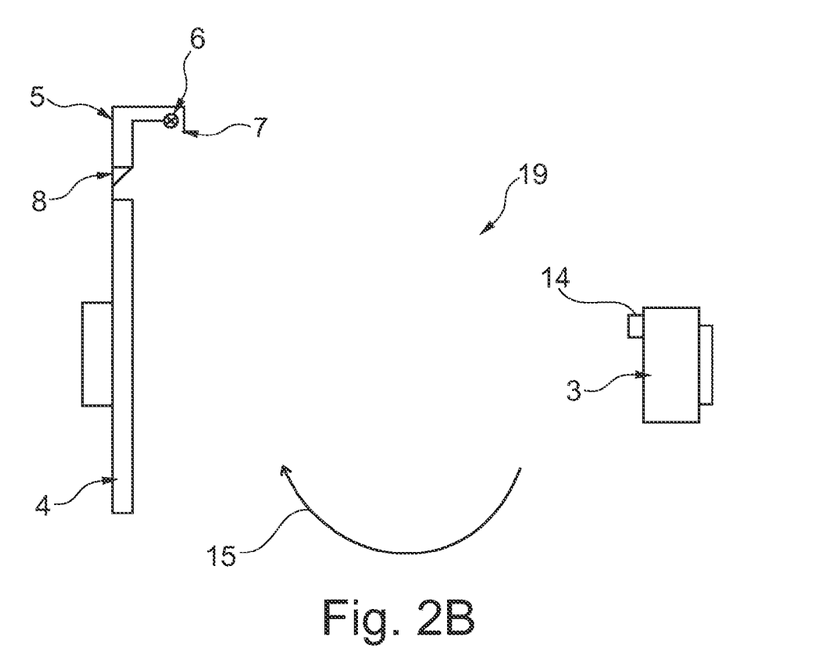

FIG. 2A further shows a calibration block 14 that has been placed in the recording area 19. The calibration block 14 can alternatively be permanently disposed in the recording area 19 of the X-ray device. The calibration block 14 can be attached permanently to, say, a housing component containing the X-ray source 3, as shown in FIG. 2B.

The calibration block 14 can be suitable for determining the position of the surface data 11 and the color data 12 relative to the radiograph 13.

The calibration block 14 might also be suitable for determining the positions of the light source 6, the masking edge 7 and the optical detector 8 relative to the X-ray device.

Furthermore, the calibration block 14 shown can be one that can be used for determining the properties of the light source 6, for example its position during rotation, and its brightness and color distribution, the properties of the masking edge 7, for example its position and shape, and the properties of the optical detector 8, for example its position, its sensitivity to color and luminous intensity, and its degree of distortion.

It is also possible to use a calibration block 14 to determine the properties of the X-ray source and the X-ray detector.

Calibration blocks known in the prior art are well-suited for determining one or more of the aforementioned parameters.

On the basis of these relative positions, it is possible to combine the radiographs 13 produced by means of the X-ray detector 4 with the surface data 11 and color data 12 acquired by the imaging unit 5. For example, a transformation matrix can be defined that combines the coordinate system of the radiograph 13 with the coordinate system of the surface data 11 and the color data 12. All of said data can then be transferred to a common coordinate system, if desired.

The radiograph 13 together with the surface data 11 and the color data 12 can be displayed jointly on a display device 18 such as a monitor. This can facilitate the interpretation of the radiograph 13.

Figure 4A:
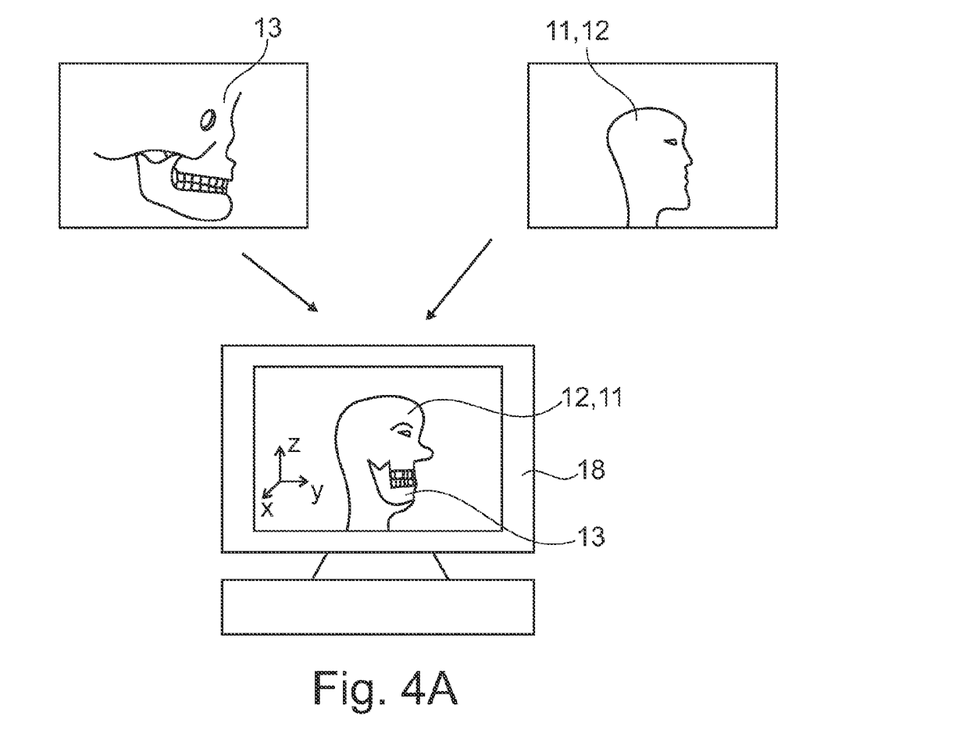
FIGS. 4A and 4B are diagrammatic representations of the acquired data.

FIG. 4A shows by way of example the manner in which color and surface data 12, 11 are displayed together with a three-dimensional radiograph 13 as a common image on a monitor, the color and surface data 12, 11 being represented in transparent form so that the radiograph 13 is at the same time also visible.

Figure 4B:
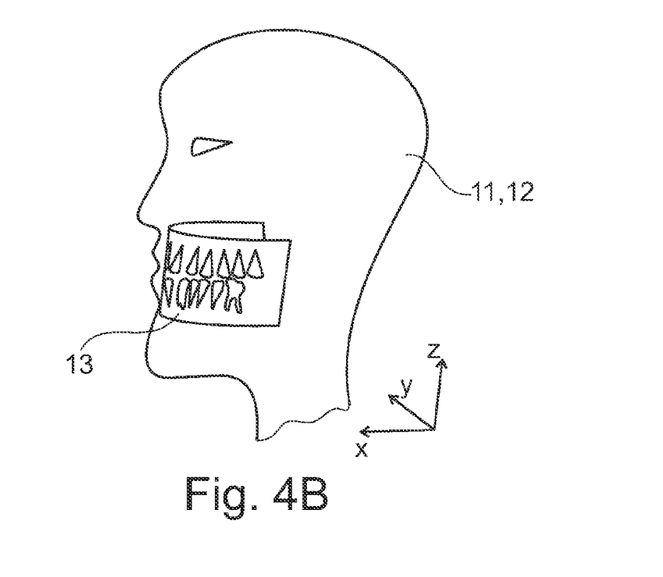

FIG. 4B diagrammatically shows the manner in which a two-dimensional radiograph 13 such as a panoramic radiograph can be displayed within the surface and color data 12, 11 displayed in transparent form.

It would also be possible to select the two-dimensional coordinate system of a tomogram as a common coordinate system and to transfer the surface data 11 and color data 12 to this two-dimensional coordinate system, for example by projection, in order to display them jointly with the radiograph 13 in the form of a tomogram.

LIST OF REFERENCE NUMERALS OR CHARACTERS 1 holder
2 supporting device/supporting arm
3 source of X-rays
4 X-ray detector
5 imaging unit
6 light source
6' bundle of light
7 masking edge
8 optical detector
9 light-colored region on the patient
10 dark-colored region on the patient
11 surface data
12 color data
13 radiograph
14 calibration block
15 direction of rotation
16 patient
17 shadow demarcation line, line between light-colored and dark-colored regions
18 display device
19 recording area
D axis of rotation

The invention claimed is:

1. A dental X-ray system, comprising:
   an X-ray source;
   an X-ray detector;
   a supporting device adapted to move the X-ray source and the X-ray detector at least partially around a recording area located between the X-ray source and the X-ray detector; and
   at least one imaging unit adapted to image the recording area, wherein the at least one imaging unit comprises:
      at least one light source adapted to produce a polychromatic bundle of light directed toward the recording area,
      at least one masking edge that extends, at least partially, into the polychromatic bundle of light between the light source and the recording area for creation of a light-colored region, a dark-colored region, and a shadow demarcation line separating the light-colored region and the dark-colored region in the recording area, and
      at least one optical detector adapted to image the light-colored region, the dark-colored region, and the shadow demarcation line,
   wherein the at least one light source, the at least one masking edge, and the at least one optical detector are disposed on at least one of the supporting device, the X-ray source, and the X-ray detector and can be moved, together with the X-ray source and the X-ray detector, around the recording area.

2. The dental X-ray system as defined in claim 1, wherein the at least one light source is comprised of one or more juxtaposed individual light sources.

3. The dental X-ray system as defined in claim 1, wherein the at least one light source has a maximum illumination intensity of 5 lm/cm$^2$.

4. The dental X-ray system as defined in claim 1, wherein the at least one optical detector registers both brightness information and color information of the recording area and produces an image.

5. The dental X-ray system as defined in claim 4, wherein in the image there is an area that is free from a shadow bounded by the shadow demarcation line to an extent of more than 50%.

6. An imaging method, comprising:
   generating X-rays by an X-ray source such that the X-rays pass through a recording area, during an at least partial rotation of a system, comprising of the X-ray source and an X-ray detector, around the recording area, the recording area being located between the X-ray source and the X-ray detector;
   recording the X-rays from a number of different directions with the X ray detector to generate a radiograph; and
   producing a light-colored region and a dark-colored region in the recording area during the at least partial rotation of the system with an imaging unit that moves simultaneously with the system, the imaging unit comprising at least one light source that emits a polychromatic bundle of light, at least one masking edge, and at least one optical detector,
   wherein the light-colored region and the dark-colored region linearly adjoin each other and form a shadow demarcation line,
   wherein at least parts of the light-colored region, the dark-colored region, and the shadow demarcation line are recorded as images by the at least one optical detector, and
   wherein color data and surface data are acquired from the images.

7. The method as defined in claim 6, wherein the images are recorded successively by the at least one optical detector during the at least partial rotation of the system.

8. The method as defined in claim 6, wherein the color data and the surface data are acquired from images recorded from at least four different directions.

9. The method as defined in claim 6, wherein the color data and the surface data are acquired from images recorded from angularly uniformly distributed directions during the at least partial rotation of the system.

10. The method as defined in claim 6, wherein images for the color data and images for the surface data are created successively at equal time intervals during the at least partial rotation of the system.

11. The method as defined in claim 6, further comprising:
    prior to creation of the images, generating a radiograph, surface data, and color data of a calibration block in the recording area of the X-ray system and determining a relative position of the color data and the surface data, of the calibration block, in relation to the radiograph of the calibration block.

12. The method as defined in claim 11, further comprising: transferring, according to the determined relative position, the color data, the surface data and the radiograph of the calibration block to a common coordinate system by a transformation.

13. The method as defined in claim 11, further comprising: displaying the color data and the surface data, acquired from the images, together with the radiograph generated in the recording step.

14. The method as defined in claim 13, wherein the color data and the surface data, acquired from the images, and the radiograph, generated in the recording step, are simultaneously displayed in a common coordinate system.

15. The method as defined in claim 6, further comprising:
    prior to creation of the images, generating a radiograph, surface data, and color data of a calibration body in the recording area of the X-ray system, and defining a color correction.

16. The method as defined in claim 6, further comprising:
    producing a geometric model of a surface of an object within the recording area from at least two of the images by a stereometric method,
    wherein the surface data acquired from the images is used in the stereometric method.

17. The method as defined in claim 16, wherein a resolution of the geometric model of the surface produced by the stereometric method is higher than a resolution of the surface data.

18. The method as defined in claim 16, wherein only an illuminated area is used in the stereometric method.

19. The dental X-ray system as defined in claim 4, wherein in the image there is an area that is free from a shadow bounded by the shadow demarcation line to an extent of more than 75%.

20. The dental X-ray system as defined in claim 4, wherein in the image there is an area that is free from a shadow bounded by the shadow demarcation line to an extent of more than 85%.

21. The dental X-ray system as defined in claim 1, wherein the at least one imaging unit is further configured to produce a plurality of images of the recording area during the at least partial movement of the X-ray source and the X-ray detector around the recording area.

* * * * *